(12) United States Patent
Fauconet et al.

(10) Patent No.: US 7,253,313 B2
(45) Date of Patent: Aug. 7, 2007

(54) METHOD FOR PURIFYING (METH)ACRYLIC ACID BY OXIDISING A GASEOUS SUBSTRATE

(75) Inventors: Michel Fauconet, Valmont (FR); Jean-Marie Destenay, Villing (FR)

(73) Assignee: Arkema France, Puteaux (FR)

( * ) Notice: Subject to any disclaimer, the term of this patent is extended or adjusted under 35 U.S.C. 154(b) by 0 days.

(21) Appl. No.: 10/577,415

(22) PCT Filed: Oct. 1, 2004

(86) PCT No.: PCT/FR2004/002482

§ 371 (c)(1),
(2), (4) Date: Apr. 26, 2006

(87) PCT Pub. No.: WO2005/049541

PCT Pub. Date: Jun. 2, 2005

(65) Prior Publication Data

US 2007/0106093 A1    May 10, 2007

(30) Foreign Application Priority Data

Nov. 4, 2003    (FR) .................................. 03 12905

(51) Int. Cl.
*C07C 51/42*    (2006.01)

(52) U.S. Cl. ..................................................... 562/600
(58) Field of Classification Search .................... None
See application file for complete search history.

(56) References Cited

U.S. PATENT DOCUMENTS

| 3,932,500 | A |   | 1/1976 | Duembgen et al. |
| 5,426,221 | A |   | 6/1995 | Willersinn |
| 5,705,688 | A | * | 1/1998 | Fauconet et al. ........... 562/600 |
| 5,780,679 | A |   | 7/1998 | Egly et al. |
| 5,780,688 | A |   | 7/1998 | Hoffmann et al. |

* cited by examiner

*Primary Examiner*—Paul A. Zucker
(74) *Attorney, Agent, or Firm*—Steven D. Boyd

(57) ABSTRACT

The present invention relates to a method for purifying (meth)acrylic acid obtained by oxidizing propane, propylene, acrolein, isobutane, isobutene, ter-butyl alcohol, (meth)acrolein and mixtures thereof by sending the gaseous reaction mixture to the bottom of a countercurrent absorption column (C1) which is supplied at the top with at least one type of hydrophobic heavy solvent, sending the flow (2) from the bottom of column (C1) to a light component separation column (C2) and sending the flow from the base of column (C2), stream (4) to a separation device made up of three sections, exhaustion (S1), concentration (S2) and rectification (S3) respectively in order to extract pure (meth) acrylic acid."

25 Claims, 2 Drawing Sheets

METHOD FOR PURIFYING (METH)ACRYLIC ACID BY OXIDISING A GASEOUS SUBSTRATE

FIELD OF THE INVENTION

The present invention fits into the context of a method for fabricating (meth)acrylic acid according to which a gas substrate (propane and/or propylene and/or acrolein in the case of acrylic acid; isobutane and/or isobutene and/or tertbutyl alcohol and/or methacrolein in the case of methacrylic acid) is oxidized by a catalytic or redox method, and the (meth)acrylic acid is recovered from the hot reaction gas mixture, by countercurrent absorption of a heavy hydrophobic solvent, said absorption being carried out in the presence of at least one polymerization inhibitor (also called stabilizer).

The invention described here describes in particular the substantially quantitative recovery, from a raw mixture of acrylic acid in the solvent previously stripped of light compounds:
- of acrylic acid (recovery yield >98.5%), the purified stream containing less than 0.5% of heavy compounds;
- of the heavy hydrophobic solvent (recovery yield >99.9%);
- of the stabilizers with boiling point <260° C. under atmospheric pressure (recovery yield >50%).

BACKGROUND OF THE INVENTION

The main method for synthesizing acrylic acid uses a reaction of catalytic oxidation of propylene with a mixture containing oxygen. This reaction is generally carried out in the vapor phase, usually in two steps, which may be carried out in two distinct reactors or a single reactor:
- the first step carries out the substantially quantitative oxidation of the propylene to an acrolein rich mixture, in which the acrylic acid is a minority component;
- the second step completes the conversion of acrolein to acrylic acid.

The gas mixture issuing from the second oxidation step consists of:
- acrylic acids;
- light compounds incondensable in the temperature and pressure conditions commonly employed (unconverted nitrogen, oxygen and propylene, propane present in the reactive propylene, carbon monoxide and dioxide formed in small quantities by final oxidation);
- light condensable compounds, particularly water, generated by the propylene oxidation reaction, unconverted acrolein, light aldehydes, such as formaldehyde and acetaldehyde, and acetic acid, the main impurity generated in the reaction section;
- heavy compounds: furfuraldehyde, benzaldehyde, maleic anhydride, etc.

A method well described in the literature for synthesizing methacrylic acid by oxidation is identical in principle to that of acrylic acid, except for the reactive substrate (which may be isobutene or tertbutanol), the intermediate oxidation product (methacrolein) and the types of light condensable byproduct compounds (the reaction gas mixture contains, among other compounds, acrylic acid in addition to the light compounds present in the reaction gas of the acrylic acid synthesis method).

The second stage of fabrication consists in recovering the acrylic acid from the hot gas mixture, previously cooled to a temperature of 150-200° C., by introducing this gas at the bottom of an absorption column where it meets a countercurrent flow of absorption solvent, which we shall refer to below by the term "solvent", introduced at the top of the column, and inside which cooling, condensation, absorption and rectification processes take place simultaneously. In most of the methods described, the solvent employed in this column is water or a high boiling point hydrophobic solvent.

The use of a heavy hydrophobic solvent in this first absorption section, as described in French patent No. 2 146 386 and German patent No. 4 308 087, has advantages over the use of water, the main one being to make the separation of the light compounds far easier, particularly water and acetic acid, which are difficult to remove in the methods with aqueous solution.

On completion of the absorption step, the known methods for recovering (meth)acrylic acid from the solutions of the monomer in the solvent involve a step of removal of the light compounds at the top of a stripping column, designed to send most of these light compounds to the preceding absorption column, where they are removed in the head effluent, as described in the two abovementioned French and German patents. For complete removal of the light compounds, it is necessary to use a distillation column for removing the final traces of these volatile impurities at the top. Other alternatives have been proposed, like the one described in European patent No. 706 986, which consists in removing the final traces of light impurities (tapping) at the top of an upper section of the final acrylic acid distillation column, the pure monomer being recovered in a tapped off side stream. A method is proposed in the French patent application filed today in the name of the present applicant and also having the title "Method for purifying (meth)acrylic acid obtained by oxidation of a gas substrate" in which the conditions of the absorption and stripping sections are selected so as to obtain a stream of raw (meth)acrylic acid stripped of most of these light impurities in a single step, without an additional column or tapping section.

The subsequent steps of the purification method, in the case of the use of a heavy hydrophobic absorption solvent, are designed to quantitatively recover the (meth)acrylic acid, to separate the heavy impurities from the solvent, and to regenerate the solvent for recycling to the absorption step. In fact, the need to recover and recycle the solvent in a sort of "loop" is necessary for economic reasons and to avoid pollutant releases, making it necessary to separate and remove the compounds heavier than acrylic acid, in order to prevent their holdup in this solvent loop. For this purpose, a sufficient quantity of these heavy compounds must be purged, at least equal to the quantity fed to the first absorption section.

Among the compounds heavier than acrylic acid, mention can be made of the impurities generated in the reaction step, and also the polymerization inhibitors introduced at each step of the purification method. In fact, since (meth)acrylic acid is a sensitive product readily prone to a polymerization process favored by the temperature, polymerization inhibitors are introduced into the purification equipment in order to avoid this process.

Numerous polymerization inhibitors are conventionally mentioned in (meth)acrylic acid purification methods. Among them, mention can be made of phenolic compounds, such as hydroquinone or methylether of hydroquinone, phenothiazine and its derivatives, such as methylene blue, quinones such as benzoquinone, manganese salts, such as manganese acetate, metal thiocarbamates such as copper salts of dithiocarbamic acid, like copper dibutyldithiocarbamate, N-oxyl compounds, including 4-hydroxy-2,2,6,6- tetramethyl-piperidinoxyl, amine compounds, such as derivatives of paraphenylene diamine, compounds with a nitroso group such as N-nitrosophenyl hydroxylamine, and ammonium salts of N-nitrosophenyl hydroxylamine.

The vast majority of polymerization inhibitors are heavier compounds than (meth)acrylic acid, and are therefore not entrained with the (meth)acrylic acid during distillation processes. Thus, these inhibitors are generally introduced at all points of the equipment (column heads, condensers, etc.) which may be the seat of a liquid-vapor equilibrium leading to the condensation of (meth)acrylic acid rich streams. The efficiency of these polymerization inhibitors, used alone or in mixtures, is generally increased if they are used in combination with the introduction of oxygen or a gas stream containing oxygen at the bottom of the column.

The polymerization inhibitors are introduced pure, if liquid, or in solution in a solvent, which is selected advantageously from the absorption solvent or (meth)acrylic acid.

The heavy compounds accumulated in the method also consist of impurities originating from side reactions in the acrylic acid synthesis step by oxidation of propylene or propane, or in the methacrylic acid synthesis step by oxidation of isobutene or isobutane. Another category of heavy impurities is that resulting from degradation reactions during the purification steps. The use of heavy hydrophobic absorption solvents with significantly higher boiling points than that of the (meth)acrylic acid requires the application of high temperature levels, particularly at the column bottom. These high temperature levels promote the degradation of the components present in the stream, for example of the solvent and the polymerization inhibitors, and accordingly demand high energy consumption, to heat the stream to boiling. The thermal levels reached by these streams poor in light compounds may be limited to a certain degree by operating the equipment under reduced pressure, but the requirements of the condensation temperature at the top of the column, which cannot be too low at the risk of generating excessive cooling costs, of column size, of condenser and vacuum generation system, which increase proportionally with the vacuum level, mean that temperatures higher than 180° C. are generally obtained in the hottest parts of the equipment. In consequence, it is preferable to limit the number of unit operations involving the boiling of solvent rich streams.

In the case of methods employing heavy hydrophobic solvents, it is necessary to distinguish the following among the heavy compounds:

"intermediate" compounds, with boiling points between that of the (meth)acrylic acid and that of the solvent. Among these compounds are impurities generated during the reaction step, such as maleic anhydride, furfuraldehyde, benzaldehyde, or polymerization inhibitors more volatile than the solvent;

"heavy" compounds which have a higher boiling point than that of the solvent, among which mention can be made of the impurities formed in the method, such as oligomers, derivatives of addition to the double bond of the (meth)acrylic acid, polymers, degradation products of the solvent or the inhibitors, and the polymerization inhibitors less volatile than the solvent.

On completion of the step to remove the residual light compounds, the (meth)acrylic acid is the most often recovered, from its mixture with the heavy solvent containing the heavier impurities, at the top of a distillation column, the less volatile compounds than the monomer being removed in the bottom stream from this column.

The removal of a sufficient quantity of heavier compounds than the solvent, in order to prevent their holdup in the method, can be completed by the use of the purge of a stream enriched with these compounds, obtained at the bottom of a solvent regeneration section, consisting in evaporating or distilling all or part of the solvent stream flowing in a loop in the method. The stream enriched with heavier compounds than the solvent is then removed at the bottom of the evaporator or of the distillation column.

However, the removal of the compounds heavier than the solvent is costly in terms of energy and is inevitably accompanied by equally costly loss of solvent, which is poorly separated from the heavier compounds, and of the polymerization inhibitors. In consequence, it is economically advantageous to limit the quantity of stream concerned by the purging of the heavy impurities.

As described in the abovementioned French patent No. 2 146 386, it is possible to separate the intermediate compounds at the bottom of a water scrubbing column, or at the top of a distillation column.

In the case of extraction using water, the method has the disadvantage of generating an additional aqueous stream laden with pollutant compounds which it is costly to treat before release, and furthermore, this method is unsuitable for removing all the heavy impurities, particularly those that are relatively nonpolar. This results in the progressive holdup of these intermediate compounds in the solvent loop, inevitably leading to their entrainment in the distilled (meth) acrylic acid.

In the other case of separation by distillation, the method also suffers from substantial disadvantages. In purification methods using absorption by heavy hydrophobic solvent, the (meth)acrylic acid concentration in the raw skimmed mixture does not exceed 30%, the remainder essentially consisting of solvent. Since the concentrations of heavy intermediate compounds are lower than that of (meth)acrylic acid, these compounds are extremely diluted in the stream consisting essentially of solvent obtained at the bottom of a (meth)acrylic acid distillation column. In consequence, the separation of small quantities of intermediate compounds in a distillation column fed with a bottom stream from the preceding distillation column, as described in French patent No. 2 146 386, requires treating a very large stream of highly diluted mixture. The drawbacks of such a method are a high loss of solvent entrained at the top of the column, costly energy consumption to heat a large quantity of heavy solvent to boiling, and considerably larger equipment size, essentially the column bottom and boiler, implying higher investment costs. Furthermore, such a method does not permit the efficient recovery of the stabilizers that are heavier or lighter than the solvent, for recycling to the columns located upstream of the method.

An improvement to the process of removing heavy intermediate impurities has been described in French patent No. 2 736 912, which claims a purification section consisting in distilling pure acrylic acid at the top of a first column, allowing little monomer to pass at the bottom, and sending the column bottom stream containing the heavy intermediate impurities to feed another column, in tapping off a side stream rich in intermediate compounds, and in recycling the acrylic acid rich column head stream to the preceding column.

This method has the disadvantage of further generating a loss of solvent and polymerization inhibitors.

SUMMARY OF THE INVENTION

The applicant company has tried to solve the problems described above of the prior art, in order significantly to improve the (meth)acrylic acid purification method with absorption by a heavy hydrophobic solvent, on the following points:
  recovery of the solvent,
  recovery of the stabilizers,
  reduction of energy consumption and equipment size,
  limitation of product losses by thermal degradation, while ensuring particularly efficient (meth)acrylic acid recovery.

For this purpose, it is proposed to send the stream obtained at the bottom of the absorption column to a separation device comprising a separation column removing the light compounds, then to three respective stripping, concentration and rectification sections, for recovering the desired pure acid, for recovering and advantageously for recycling the heavy hydrophobic solvent or solvents to the absorption column, and separating from the desired (meth)acrylic acid the heavy intermediate compounds including the stabilizers, this stream—with a low concentration of desired (meth)acrylic acid—which can advantageously be treated in a downstream distillation column.

The following operations are carried out in this small-sized column:
  removal of the heavy intermediate compounds at the top of the column, in sufficient quantity to prevent their holdup in the solvent loop, in a stream with a low concentration of solvent and stabilizer; and
  at the bottom of the column, recovery of most of the solvent and stabilizer initially present in the column feed, for recycling as a stabilizing stream at the top of the preceding columns of the recovery method.

DETAILED DESCRIPTION OF THE INVENTION

Figure 1:
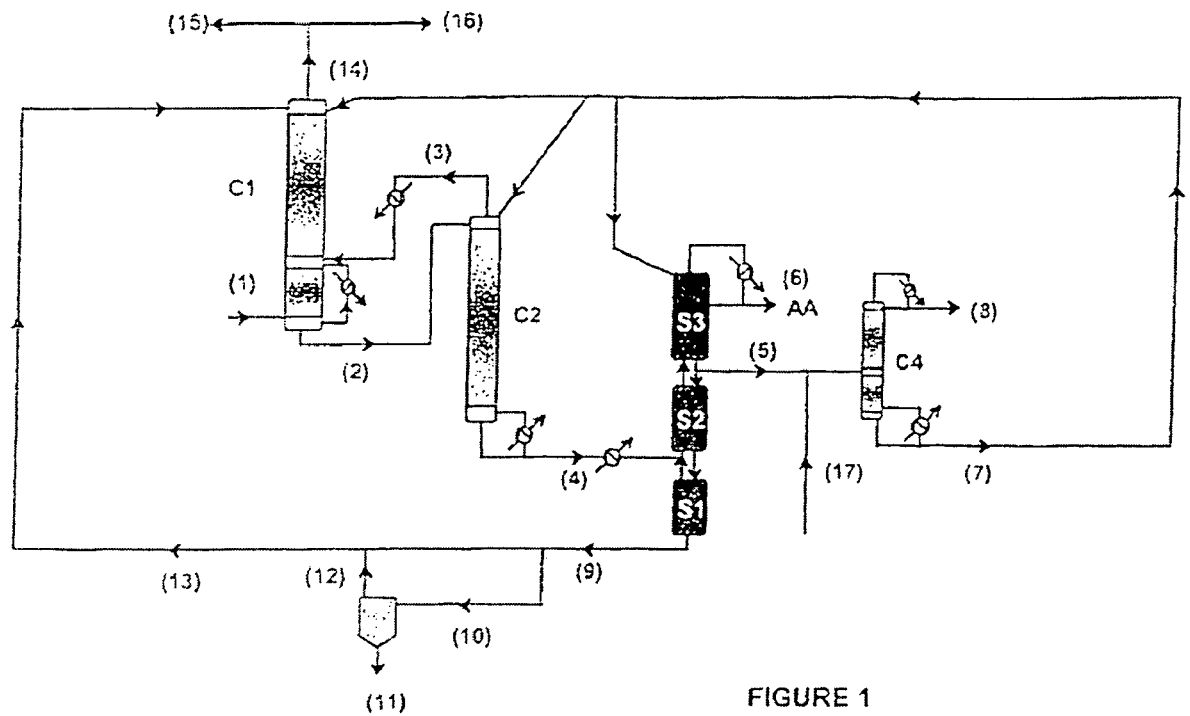
FIG. 1 is a schematic flow sheet of a preferred embodiment of the invention.

The subject of the present invention is therefore a method for purifying (meth)acrylic acid obtained by catalytic or redox oxidation, of a gas substrate consisting of propane and/or propylene and/or acrolein in the case of the fabrication of acrylic acid, and of isobutane and/or isobutene and/or tertbutyl alcohol and/or methacrolein in the case of the fabrication of methacrylic acid, said gas mixture mainly consisting of:
  propane and/or propylene or isobutane and/or isobutene if previously contained by the substrate;
  final oxidation products;
  the desired (meth)acrylic acid;
  (meth) acrolein;
  tertbutyl alcohol in the case of the fabrication of methacrylic acid;
  water vapor;
  acetic acid with, in the case of the fabrication of methacrylic acid, acrylic acid as a byproduct; and
  heavy products of side reactions, according to which the reaction gas mixture is sent to the bottom of an absorption column (C1) which is supplied at the top and in countercurrent with at least one heavy hydrophobic absorption solvent, the absorption taking place in the presence of at least one polymerization inhibitor to obtain:
  at the top of the column (C1) a gas stream consisting of:
    light incondensable compounds (that is, incondensable in standard pressure and temperature conditions) consisting of propane and/or propylene or isobutane and/or isobutene, according to whether acrylic acid or methacrylic acid is fabricated and the products of the final oxidation of the mixture;
    major quantities of light condensable compounds consisting of water and acetic acid in the case of the fabrication of acrylic acid, or of water, acetic acid and acrylic acid in the case of the fabrication of methacrylic acid; and
    (meth)acrolein;
  at the bottom of said column (C1), a stream consisting of:
    (meth)acrylic acid;
    the heavy absorption solvent or solvents;
    the heavy products of side reactions;
    the polymerization inhibitor or inhibitors; and
    minor quantities of said light condensable compounds, the stream issuing from the column (C1) is then sent to a separation column (C2) in which a separation is carried out to obtain:
  at the top, a stream consisting of light impurities which are sent to the bottom part of the absorption column (C1); and
  at the bottom, a stream consisting of:
    (meth)acrylic acid in solution in the absorption solvent or solvents;
    a small proportion of said light condensable compounds;
    the heavy products of side reactions; and
    the polymerization inhibitor or inhibitors, characterized in that the liquid stream from the bottom of the column (C2) is sent as feed to the top of a first separation section (S1) suitable for obtaining
  at the top, a gas stream; and
  at the bottom, a stream essentially containing the absorption solvent or solvents stripped of the lighter compounds, said stream being recycled as feed to the column (C1) directly or after removal of some of the heavy products contained in this stream;

said gas stream obtained at the top of the first section (S1), or the liquid stream generated by the condensation of this gas, being sent to the bottom of a second separation section (S2) suitable for concentrating the intermediate heavy compounds of which the boiling point is between that of the solvent (or of the lowest boiling point solvent in the case of a solvent mixture) and that of (meth)acrylic acid, and suitable for obtaining:
  at the top, a gas stream; and
  at the bottom, a liquid stream that is sent to the top of the first section (S1), said gas stream obtained at the top of the second section (S2), or the liquid stream generated by condensation of this gas, being sent to the bottom part of a third separation section (S3) suitable for obtaining:

at the top, a gas stream which is condensed and partly recycled to the top of said section (S3), the remainder being tapped off as pure (meth)acrylic acid stripped of the heavy impurities; and at the bottom, a liquid stream which is sent to the top of the second section (S2).

The sections (S1), (S2) and (S3) can be qualified respectively as the lower stripping section, the intermediate section for concentration of heavy intermediate compounds, and the upper rectification section.

The purification according to the present invention thus takes place in three successive sections S1, S2 and S3. These three sections have the common feature that they are the seat of unit operations involving at least one liquid-gas separation stage. In these separation operations, a (vaporized) liquid mixture and/or a (condensed) gas mixture containing compounds of different volatilities generate a vapor that is richer in the most volatile compounds and a liquid that is richer in the least volatile compounds. These separation operations can be carried out in any unit combining conventional distillation equipment: any type of distillation column, and any type of evaporator, boiler and condenser.

According to a first embodiment of the method of the invention—which is described in greater detail below with reference to FIG. 2—the sections (S1), (S2) and (S3) are the respectively lower, intermediate and upper sections of the same column (C3), the stream at the bottom of the column (C2) being sent to the column (C3) above the section (S1).

In this case, the number of theoretical trays of the column (C3) is advantageously 8 to 25, particularly 10 to 20, the number of theoretical trays of each of the sections (S1), (S2) and (S3) of the column (C3) being advantageously respectively:

1 to 5, particularly 1 to 3;
1 to 10, particularly 1 to 5; and
3 to 20, particularly 5 to 15.

The pressure at the top of the column (C3) is advantageously 2.7 to 27 kPa (20 to 202 torr), preferably 6.7 to 24 kPa (50 to 180 torr).

The temperature of the bottom of the column (C3) is advantageously 150 to 250° C., preferably 180 to 230° C., and the temperature of the top of said column (C3) is advantageously 40 to 110° C. preferably 65 to 95° C.

Preferably, the column (C3) is a distillation column provided with a bottom boiler, a top condenser, with a reflux rate $T_R$ imposed at the top of 0.5/1 to 4/1, preferably of 0.5/1 to 2/1, because a large number of separation stages is necessary to obtain a (meth)acrylic acid of sufficient purity.

According to a second embodiment of the method of the invention—which is described in greater detail below with reference to FIG. 3—the sections (S1) and (S2) are the respectively lower and upper sections of the same column $(C3_1)$, the stream from the bottom of the column (C2) being sent to the column $(C3_1)$ above the section (S1), and the section (S3) is the single section of a column $(C3_2)$ supplied at its bottom with the stream from the top of the column $(C3_1)$.

The pressure at the top of the column $(C3_1)$ is advantageously 2.7 to 27 kPa (20 to 202 torr), preferably 4 to 15 kPa (30 to 112 torr), and the pressure at the top of the column $(C3_2)$ is advantageously 2.7 to 27 kPa (20 to 202 torr), preferably 6.7 to 24 kPa (50 to 180 torr).

The temperature at the bottom of each of the columns $(C3_1)$ and $(C3_2)$ is advantageously 150 to 250° C., preferably 170 to 210° C., and the temperature at the top of each of said columns $(C3_1)$ and $(C3_2)$ is advantageously 40 to 110° C., preferably 60 to 90° C.

According to a third embodiment of the method of the invention—which is described in greater detail below with reference to FIG. 4—the sections (S1) and (S2) are each formed from at least one evaporator, the stream from the bottom of the column (C2) being sent as feed to the evaporator (E1) or to a first evaporator $(E1_1)$ of a plurality of evaporators mounted in series of the section (S1), the stream containing the absorption solvent or solvents stripped of the lighter compounds being obtained at the bottom of the evaporator (E1) or of the last evaporator $(E1_2)$ of the series $(E1_1; E1_2)$ of the section (S1), and the section (S3) is the single section of a column $(C3_3)$ supplied at its bottom with the stream from the top of the evaporator (E2) or from the last evaporator $(E2_2)$ of a plurality of evaporators mounted in series of the section (S2).

The pressure at the top of the column $(C3_3)$ is advantageously 2.7 to 27 kPa (20 to 202 torr), particularly 6.7 to 24 kPa (50 to 180 torr).

The temperature at the bottom of column $(C3_3)$ is advantageously 150 to 250° C., preferably 170 to 210° C., and the temperature at the top of said column $(C3_3)$ is advantageously 40 to 110° C., preferably 60 to 90° C.

According to a particular feature of the method of the invention, the (meth)acrylic acid concentration in the feed to the section (S1) is 5 to 70% by weight, particularly 10 to 30% by weight.

According to a further particular feature of the method of the invention, the stream of heavy intermediate compounds from the bottom of the section (S3) is sent to a column (C4) adapted for removing, at the top, at least part of the heavy intermediate compounds, and for recovering, at the bottom, a stream of the heavy solvent or solvents and of the polymerization inhibitor or inhibitors initially present in the stream fed to the column (C4), said stream being advantageously recycled as a stabilizing stream at the top of the preceding columns or sections (C1; C2; C3; $C3_1$; $C3_2$, $C3_3$).

The pressure at the top of the column (C4) is advantageously 2.7 to 40 kPa (20 mmHg to 300 mmHg), particularly 9.3 to 20 kPa (70 mmHg to 150 mmHg).

The stream from the bottom (9) of the section (S1) is advantageously recycled to the top of the absorption column (C1), if necessary after removing a stream of heavy impurities having a boiling point higher than that of the solvent or higher than that of the solvent having the highest boiling point.

To offset the losses occurring during the purification sequence, fresh solvent or solvents are introduced into the solvent rich loops, particularly into the stream of the bottom of the section (S1) and of the column (C4) recycled at the top of the column (C1). In the case in which this solvent contains light impurities with a boiling point close to that of the (meth)acrylic acid, it could be particularly advantageous to supply the solvent complement to the stream feeding the column (C4), in order to remove these light impurities which are difficult to separate from the (meth)acrylic acid.

According to the present invention, one or more heavy hydrophobic absorption solvents is advantageously used having a boiling point under atmospheric pressure of more than 200° C., ditolylether being particularly preferred as a heavy hydrophobic solvent. The patent literature offers many examples of heavy hydrophobic solvents.

The polymerization inhibitor or inhibitors in the presence of which the absorption is carried out in the column (C1) and the separations are carried out in the column (C2) and the sections (S1) to (S3) are selected in particular from those indicated above.

FIG. 1 in the drawing appended hereto shows a general flowchart of the (meth)acrylic acid purification method according to the invention, involving the three sections S1, S2 and S3 described above, FIGS. 2 to 4 respectively showing the three particular embodiments described above by the more precise representation of the assembly of sections S1, S2 and S3.

With reference to FIG. 1, applied to the synthesis of acrylic acid, it may be observed that the reaction gas mixture issuing from the oxidation of propylene and acrolein, mainly consisting of:

On the one hand, incondensable compounds in the operating pressure conditions of the column: propylene, final oxidation products ($CO$, $CO_2$), On the other, condensable compounds: acrylic acid, acrolein, water, acetic acid, heavier products of side reactions in very small quantities, is sent (stream 1) to the bottom of absorption column C1 fed at the top and in countercurrent with a heavy hydrophobic solvent recovered in the final steps of the method (stream 13: solvent at boiling point higher than 200° C. under atmospheric pressure).

The stream 2 obtained at the bottom of the column C1 mainly consists of acrylic acid and solvent, and also small amounts of acetic acid, water and acrolein. This stream is then stripped of these light impurities by sending it to a distillation column C2 where they are concentrated at the top, in a mixture with acrylic acid and traces of solvent. The gas stream obtained at the top of the column C2 is condensed in a heat exchanger and sent to column C1 (stream 3). The stream 4 obtained at the bottom of the column C2 then consists mainly of acrylic acid in a solution in the solvent, and heavy impurities, issuing from side reactions, present in small quantities in the reaction gas stream.

The gas stream 14 entrained at the top of column C1 contains the compounds initially present in the reaction gas and not absorbed: incondensable products at the operating pressure of the column (propylene, $CO$, $CO_2$), water, acrolein, acetic acid. Most of this stream 14 is advantageously recycled to the reaction step (stream 15) to convert the noble reagents that it contains, and this stream (stream 16) can also be purged slightly to prevent holdup in the loop thus formed from the incondensable compounds resulting from the final oxidation of propylene ($CO$, $CO_2$) and nitrogen from the air introduced in the reaction step. According to a slightly different embodiment, the stream 14 can also be stripped of part of the water and impurities that it contains by low temperature condensation of the vapors, before being partially recycled to the reaction step and removed by incineration.

The stream 4, consisting of (meth)acrylic acid in solution in the solvent and heavier impurities than the acrylic monomer, is then sent to a set of three sections, each element S1, S2, S3 of this set optionally forming a separate element (column, evaporators or series of evaporators):

a lower stripping section S1 for recovering most of the solvent present in the stream 4, stripped of the (meth)acrylic acid and of a quantity of impurities and stabilizers belonging to the group of heavy intermediate compounds, sufficient to prevent their holdup in the loop formed of the streams 2, 4 and 13. This stream 4 is introduced into the column C1 at a place located above this section S1;

an intermediate concentration section S2, in which the impurities and stabilizers belonging to the group of heavy intermediate compounds (with boiling points between that of the solvent and that of the (meth)acrylic acid) are concentrated for their removal in a side stream 5 tapped off at a level located above section S2;

an upper rectification section S3, at the top of which the (meth)acrylic acid, stripped of most of the heavier impurities, is obtained (stream 6).

The stream 5 tapped off the bottom of section S3 is sent as a feed to a column C4 for recovery of most of the solvent and stabilizers belonging to the group of heavy intermediate compounds (stream 7 tapped off at the bottom of column C4) and for removing the heavy intermediate compounds at the top of the column (stream 8).

According to a particularly advantageous embodiment, the fresh solvent introduced into the purification loop to offset the slight losses sustained along the purification chain is introduced as a feed to the column C4 (stream 17), to strip this solvent of the possible presence of lighter impurities in the stream 8 tapped off at the top of column C4.

The stream 7 rich in solvent and stabilizer could advantageously be recycled to one or more of the columns C1, C2 and the set of sections S1 to S3.

Finally, part of the stream 9 tapped off the bottom of section S1 (stream 10) could, if necessary, be sent to an apparatus for removing the heavy impurities having a boiling point higher than that of the solvent in a stream 11, and the regenerated solvent (stream 12) can be sent, with the untreated part of the stream 9, as feed to the absorption column (stream 13). This step of deconcentration of the heavy impurities can be carried out in any apparatus for a course separation of compounds with a much higher boiling point than that of the solvent, for example in a distillation column or, more advantageously, any type of evaporator.

Figure 2:
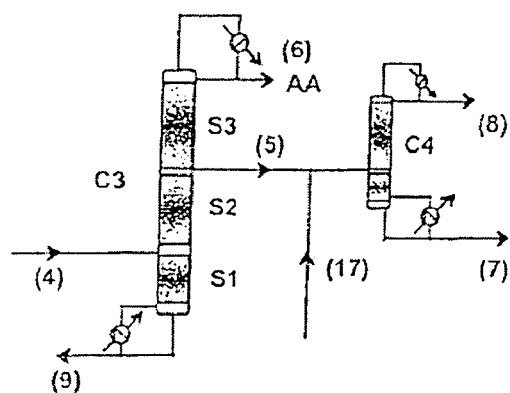
FIG. 2 is schematic flow sheet of an alternate embodiment of S1, S2, S3 and C4 of FIG. 1.

FIG. 2 shows that a column C3 can by itself accommodate the sections S1, S2 and S3.

Figure 3:
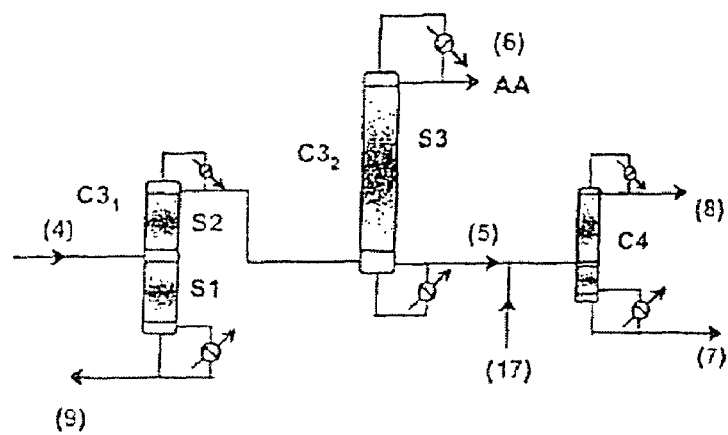
FIG. 3 is schematic flow sheet of an alternate embodiment of S1, S2, S3 and C4 of FIG. 1.

FIG. 3 shows a column $C3_1$ accommodating the sections S1 and S2 and a column $C3_2$ accommodating section S3. The head stream of column $C3_1$ feeds the column $C3_2$ at the bottom.

Figure 4:
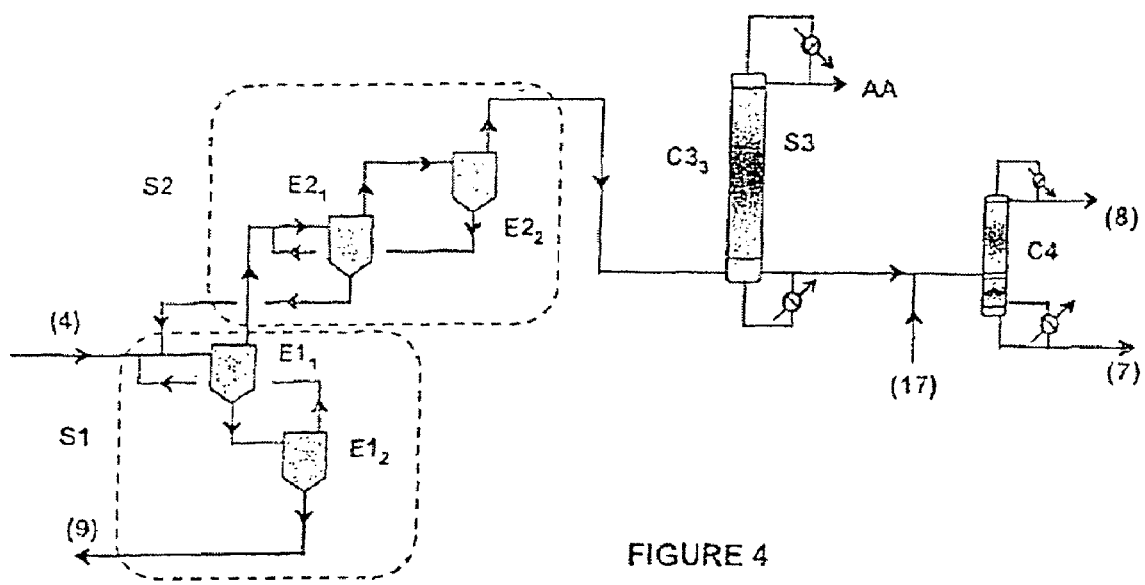
FIG. 4 is schematic flow sheet of an alternate embodiment of S1, S2, S3 and C4 of FIG. 1.

FIG. 4 shows that the section S1 comprises two evaporators in series ($E1_1$, $E1_2$), the stream 4 feeding the first evaporator $E1_1$ at the top, the bottom stream of the evaporator $E1_1$ feeding the second evaporator $E1_2$ at the top, and the bottom stream of the evaporator $E1_2$ constituting the stream 9; and the section S2 comprises two evaporators in series ($E2_1$, $E2_2$), the head stream of the evaporator $E1_1$ feeding the evaporator $E2_2$ at the top and the head stream of the evaporator $E2_1$ feeding the evaporator $E2_2$ at the top. The head stream of the evaporator $E2_2$ feeds the column $C3_3$ which accommodates the section S3.

The head stream of column $E1_2$ and the bottom stream of column $E2_1$ are recycled to the feed (4) of the evaporator $E1_1$. The bottom stream of the evaporator $E2_2$ is recycled to the feed of the evaporator $E2_1$.

The distillation columns C1, C2, C3, $C3_1$, $C3_2$, $C3_3$ and C4 may be of any type (perforated trays with or without downcomers, bubble caps, structured or bulk packing). They may be equipped with any type of boiler (vertical or horizontal heat exchangers, with thermosyphons or forced circulation, film evaporators of any type, etc.). The condensers of any type may be vertical or horizontal.

The evaporators $E1_1$, $E1_2$, $E2_1$, $E2_2$ may be of any type: evaporators with vertical or inclined tubes, plates, forced circulation, rotating film, stirred film, scraped film.

Preferably, the column accommodating section S3 (C3, $C3_2$, $C3_3$) should be equipped with a stabilizer feed at the top and at the gas inlet in the head condenser. Condensation of the vapors of the head of the column C2 could also advantageously be protected from polymerization reactions by the introduction of stabilizers at the condenser inlet. The concentration of stabilizers in the solvent stream flowing in a loop in the columns C1, C2 and the set of sections S1 to S3 of the purification method should be maintained at a sufficient value, if necessary by external addition of fresh stabilizer, in order to prevent polymerization reactions. This addition can be made at any point of the method. To prevent the generation of polymers, oxygen may be added in pure or diluted (air) form at the bottom of the columns operating under reduced pressure and containing (meth)acrylic acid. In a particularly advantageous manner, the introduction of oxygenated streams into the column C3 is carried out at a level located between the bottom of the column and the side drawoff point, preferably between the boiler and the main feed.

EXAMPLES

The examples described below illustrate the invention. The percentages are indicated as mass percentages. In these examples, the following abbreviations have been used:
AA: acrylic acid;
DTE: ditolylether;
EMHQ: methyl ether of hydroquinone Example 1

This example describes one possible operation of a single column C3. The experimental rig consists of a distillation column equipped with a bottom boiler, a top condenser, and a side outlet for tapping off part of the liquid passing through a tray located between the feed tray and the column head. The distillation operation is carried out under a reduced pressure of 13300 Pa (100 mmHg).

The liquid stream fed continuously to the column is a synthetic mixture faithfully representing the composition of a raw acrylic acid stream obtained on completion of the absorption-tapping step (bottom of column C2) of a method as shown in FIG. 1 appended hereto:
DTE: 81.74%
AA: 18.1%
maleic anhydride: 0.266
acetic acid: 0.018%
furfuraldehyde: 0.005%
benzaldehyde: 0.003%
EMHQ: 0.127%.

This column, 130 cm high, comprises a bottom section equipped with 4 downcomer-type trays with an inside diameter of 35 mm and an upper section with 16 downcomer-type trays with an inside diameter of 25 mm. The unit has an efficiency of 15 theoretical trays. The feed stream (500 g/h) is preheated to 115° C. through a heat exchanger. The feed of the column is supplied between the $2^{nd}$ and $3^{rd}$ trays of the lower section of the column, numbered from the bottom, and part of the descending liquid stream is tapped off at the side at the top tray of the bottom section. To prevent polymerization reactions, EMHQ is introduced at the top of the column, and air is injected at a rate of 1 liter/h, at the level of the tray receiving the feed.

The vapors are condensed at the top and part of the condensed liquid stream (180 g/h) is sent to the top of the column, while the distillate (96 g/h) is tapped off. The pure product obtained essentially contains acrylic acid, impurities being limited to 0.1% of maleic anhydride, 0.1% of acetic acid, and less than 0.01% of furfuraldehyde, benzaldehyde and benzoic acid.

The side liquid stream tapped off (5.4 g/h), at a temperature of 142° C., is composed of:
DTE: 58.3%
EMHQ: 7.8%
maleic anhydride: 20.5%
acrylic acid: 11.4%
benzoic acid: 1.5%
benzaldehyde: 0.4%
furfuraldehyde: 0.1%.

The column bottom stream is tapped off at a temperature of 210° C. It contains 0.01% of acrylic acid, and the acrylic acid recovery yield is higher than 99%.

Example 2

This example illustrates the operation of the recovery column C4 as described in the diagram in FIG. 1 appended hereto.

The column, equipped with a thermosyphon boiler at the bottom and a head condenser, is composed of 8 downcomer-type perforated trays with inside diameter 25 mm. The feed stream issuing from the side drawoff from a column C3, is sent at a rate of 125.5 g/h, to the boiler of the column C4. It consists of:
DTE: 65%
maleic anhydride: 17%
AA: 12.4%
EMHQ: 4.2%
benzoic acid: 1.1%
furfuraldehyde: 0.17%
benzaldehyde: 0.13%.

Since the operating pressure is 13300 Pa (100 mmHg), 37 g/h of liquid stream condensed at the column head is tapped off, at a temperature of 107° C., applying a reflux/flow ratio of 5/1. At the column bottom, 88.5 g/h of liquid stream is recovered at a temperature of 195° C.

The recovery rate of noble products reaches 97% for DTE, 78% for EMHQ and 6% for AA. The impurity removal efficiency is 89% for maleic anhydride, 94% for furfuraldehyde, 97% for benzaldehyde, and 27% for benzoic acid.

By considering the performance of each of the columns C3 and C4 described in the preceding two examples, it is possible to calculate the total recovery yields of the entire purification section of the method described in FIG. 1. Related to the raw AA stream issuing from the step of absorption by the heavy solvent, or the feed stream of the column C3, the solvent and stabilizer recovery yields respectively reached 99.98% and 85.6%, while the loss of AA in the head stream of column C4 remains limited to 0.6% of the AA initially present in the raw AA.

Example 3

This example describes one possible operation of a separation unit involving two columns $C3_1$ and $C3_2$ in series (FIG. 3). The rig consists of a first column $C3_1$ operating under a pressure of 11700 Pa (80 mmHg) equipped with 4 perforated trays each provided with a downcomer (or 3 theoretical trays), a thermosyphon boiler at the bottom, a head condenser, fed between the $2^{nd}$ and $3^{rd}$ tray using a pump (490 g/h) by a mixture with the characteristic composition of the medium (raw acrylic acid) obtained at the bottom of the preceding column C2:
DTE: 79.83%
AA: 19.8%
maleic anhydride: 0.172%
furfuraldehyde: 0.022%

EMHQ: 0.146%

At the top of the column $C3_1$, part of the condensed stream is sent to the upper tray, with a reflux rate (flow of liquid refluxed/flow of liquid tapped off) of 0.2/1. The temperature measured at the boiler is 180° C., and the head temperature reaches 119° C. The stream obtained at the bottom of the column contains 0.082% of AA, indicating a monomer recovery rate of 99.7% at the top of the column.

The stream tapped off at the top of the column $C3_1$ (120.7 g/h) mainly contains 19% of DTE, 80.15% of AA, 0.63% of maleic anhydride, 0.064% of furfuraldehyde, 0.07% of EMHQ, is sent by a pump at the $4^{th}$ tray (counted from the bottom) of a second column $C3_2$, equipped with 16 perforated trays provided with downcomers (12 theoretical trays). This column $C3_2$ is equipped at the bottom with a thermosyphon boiler, at the top of a condenser, operates under a pressure of 22600 Pa (170 mmHG) and receives a mixture of stabilizer (EMHQ in a 5% concentration in AA) at the top. The reflux rate applied at the top (flow of liquid refluxed/flow of liquid tapped off) is 1.5/1. The bottom temperature is 187° C., and the top temperature is 93° C.

The pure acrylic acid obtained at the top of the column contains 99.87% of AA and only 325 ppm of furfuraldehyde, 100 ppm of maleic anhydride, and no trace of DTE is detected. The bottom stream, in addition to DTE, contains 4.12% of AA (total AA recovery rate in both columns: 98.7%), 2.62% of maleic anhydride and 0.17% of furfuraldehyde.

The invention claimed is:

1. A process for the purification of (meth)acrylic acid from reaction gases obtained by catalytic or redox oxidation of a gas selected from the group consisting of propane, propylene, acrolein, isobutane, isobutene, tertbutyl alcohol, (meth) acrolein and mixture thereof, via extraction in a countercurrent washing of the reaction gases in an extraction column (C1) with at least one heavy hydrophobic solvent fed to the top of the extraction column (C1) and said reaction gases fed to the bottom of said extraction column (C1), characterized in that:

said extraction takes place in the presence of at least one polymerization inhibitor:

a separation of the stream (2) obtained at the bottom of the extraction column (C1), which contains the heavy hydrophobic solvent, (meth)acrylic acid and the at least one polymerization inhibitor, is conducted in separation column (C2) whereby a top stream (3) comprising light impurities is sent to the bottom part of the absorption column (C1) and a bottom stream (4) comprising (meth)acrylic acid, heavy hydrophobic solvent and the at least one polymerization inhibitor is sent to the top of a first separation section (S1):

a separation of stream (4) in first separation section (S1) forms a top gas stream and a bottom stream (9) containing the heavy hydrophobic solvent stripped of the lighter compounds, said stream being recycled as feed to extraction column (C1) directly or after removal of the heavy products contained in stream (9);

said gas stream obtained at the top of the first section (S1), or a liquid stream generated by the condensation of said gas stream, being sent to the bottom of a second separation section (S2) suitable for concentrating the intermediate heavy compounds of which the boiling point is between that of the one heavy hydrophobic absorption solvent and that of (meth)acrylic acid, and suitable for obtaining a top gas stream and a bottom liquid stream that is sent to the top of the first section (S1):

said gas stream obtained at the top of the second separation section (S2), or the liquid stream generated by condensation of said gas, being sent to the bottom part of a third separation section (S3) suitable for obtaining a top gas stream which is condensed and partly recycled to the top of said separation section (S3), the remainder being recovered as substantially pure (meth) acrylic acid stripped of the heavy impurities and a bottom liquid stream which is sent to the top of the second separation section (S2).

2. The method as claimed in claim 1, characterized in that separation sections (S1), (S2) and (S3) are respectively the bottom, intermediate and upper sections of the same column (C3), the stream (4) from the bottom of the column (C2) being sent to the column (C3) above separation section (S1).

3. The method as claimed in claim 2, characterized in that the number of theoretical trays of the column (C3) is 8 to 25, the number of theoretical trays of section (S1) is 1 to 5, of section (S2) is 1 to 10 and of section (S3) is 3 to 20.

4. The method as claimed in claim 2, characterized in that the pressure at the top of the column (C3) is 2.7 to 27 kPa, the temperature of the bottom of the column (C3) is 150 to 250° C., and the temperature of the top of said column (C3) is 40 to 110° C.

5. The method as claimed in claim 2, characterized in that the column (C3) is a distillation column provided with a bottom boiler, a top condenser, with a reflux rate $T_R$ imposed at the top of 0.5/1 to 4/1.

6. The method as claimed in claim 1, characterized in that separation sections (S1) and (S2) are the respectively lower and upper sections of the same column ($C3_1$), the stream (4) from the bottom of the column (C2) being sent to the column ($C3_1$) above separation section (S1), and separation section (S3) is the single section of a column ($C3_2$) supplied at its bottom with the stream from the top of the column ($C3_1$).

7. The method as claimed in claim 6, characterized in that the pressure at the top of the column ($C3_1$) is 2.7 to 27 kPa, the pressure at the top of the column ($C3_2$) is 2.7 to 27 kPa, the temperature at the bottom of each of the columns ($C3_1$) and ($C3_2$) is 150 to 250° C., and the temperature at the top of each of the columns ($C3_1$) and ($C3_2$) is 40 to 110° C.

8. The method as claimed in claim 1, characterized in that separation sections (S1) and (S2) are each formed from at least one evaporator, the stream (4) from the bottom of the column (C2) being sent as feed to the evaporator (E1) or to a first evaporator ($E1_1$) of a plurality of evaporators mounted in series of separation section (S1), the stream (9) containing the absorption solvent or solvents stripped of the lighter compounds being obtained at the bottom of the evaporator (E1) or of the last evaporator ($E1_2$) of the series of evaporators ($E1_1$; $E1_2$) of separation section (S1), and separation section (S3) is the single section of a column ($C3_3$) supplied at its bottom with the stream from the top of the evaporator (E2) or from the last evaporator ($E2_2$) of a plurality of evaporators mounted in series of the section (S2).

9. The method as claimed in claim 8, characterized in that the pressure at the top of the column ($C3_3$) is 2.7 to 27 kPa, the temperature at the bottom of column ($C3_3$) is 150 to 250° C., and the temperature at the top of said column ($C3_3$) is 40 to 110° C.

10. The method as claimed in claim 1, characterized in that the (meth)acrylic acid concentration in the feed to the section (S1) is 5 to 70% by weight.

11. The method as claimed in claim 1, characterized in that the stream (5) of heavy intermediate compounds from the bottom of separation section (S3) is sent to a column (C4) for removing, at the top, at least part of the heavy intermediate compounds, in a stream (8), and for recovering, at the bottom, a stream (7) of the heavy solvent or solvents and of the polymerization inhibitor or inhibitors initially present in the stream (5) fed to the column (C4), said stream (7) being recycled as a stabilizing stream at the top of the preceding columns or separation sections.

12. The method as claimed in claim 11, characterized in that the pressure at the top of the column (C4) is 2.7 to 40 kPa.

13. The method as claimed in claim 1, characterized in that the stream (9) from the bottom of separation section (S1) is recycled to the top of the absorption column (C1), optionally after removing a stream (11) of heavy impurities having a boiling point higher than that of the solvent.

14. The method as claimed in claim 1, characterized in that heavy absorbent solvent or solvents are introduced into streams 5, 7 and/or 9.

15. The method as claimed in claim 1, characterized in that the at least one heavy hydrophobic solvents has a boiling point above 200° C. at atmospheric pressure.

16. The method as claimed in claim 15, characterized in that ditolylether is used as a heavy hydrophobic solvent.

17. The method as claimed in claim 1, characterized in that the polymerization inhibitor is selected from phenolic compounds, quinones, manganese salts, metal thiocarbamates N-oxyl compounds, amine compounds, compounds with a nitroso group, and ammonium salts of N-nitrosophenyl hydroxylamine.

18. The method as claimed in claim 2, characterized in that the number of theoretical trays of column (C3) is 10 to 20, the number of theoretical trays of section (S1) is 1 to 3, of section (S2) is 1 to 5 and of section (S3) is 5 to 15.

19. The method as claimed in claim 2, characterized in that the pressure at the top of column (C3) is 6.7 to 24 kPa, the temperature of the bottom of column (C3) is 180 to 230° C., and the temperature of the top of column (C3) is 65 to 95° C.

20. The method as claimed in claim 8, characterized in that the pressure at the top of column (C3) is 6.7 to 24 kPa, the temperature of the bottom of column (C3) is 170 to 210° C., and the temperature of the top of column (C3) is 60 to 90° C.

21. The method as claimed in claim 2, characterized in that the column (C3) is a distillation column provided with a bottom boiler, a top condenser, with a reflux rate $T_R$ imposed at the top of 0.5/1 to 2/1.

22. The method as claimed in claim 6, characterized in that the pressure at the top of the column ($C3_1$) is 4 to 15 kPa, the pressure at the top of the column ($C3_2$) is 6.7 to 24 kPa, the temperature at the bottom of each of the columns ($C3_1$) and ($C3_2$) is 170 to 210° C., and the temperature at the top of each of the columns ($C3_1$) and ($C3_2$) is 60 to 90° C.

23. The method as claimed in claim 1, characterized in that the (meth)acrylic acid concentration in the feed to the section (S1) is 10 to 30% by weight.

24. The method as claimed in claim 11, characterized in that the pressure at the top of the column (C4) is 9.3 to 20 kPa.

25. The method as claimed in claim 1 characterized on that the polymerization inhibitor is selected from hydroquinone, methylether of hydroquinone, benzoquinone, phenothiazine and its derivatives, manganese acetate, copper salts of dithiocarbamic acid, copper dibutyldithiocarbamate, 4-hydroxy-2,2,6,6-tetramethylpiperidinoxyl, derivatives of paraphenylene diamine or N-nitrosophenyl hydroxylamine.

* * * * *